United States Patent [19]

Müller

[11] Patent Number: 5,379,629

[45] Date of Patent: Jan. 10, 1995

[54] METHOD AND APPARATUS FOR REGULATING THE CARRIER GAS PRESSURE FOR SEPARATION COLUMN ARRANGEMENTS IN GAS CHROMATOGRAPHY

[75] Inventor: Friedhelm Müller, Linkenheim, Germany

[73] Assignee: Siemens Aktiengesellschaft, Munich, Germany

[21] Appl. No.: 743,363

[22] PCT Filed: Feb. 16, 1989

[86] PCT No.: PCT/DE89/00089

§ 371 Date: Oct. 15, 1991

§ 102(e) Date: Oct. 15, 1991

[87] PCT Pub. No.: WO90/09585

PCT Pub. Date: Aug. 23, 1990

[51] Int. Cl.6 .............................................. G01N 30/32
[52] U.S. Cl. ..................................... 73/23.27; 73/23.42
[58] Field of Search ................. 73/23.42, 23.35, 23.41, 73/23.22, 23.24, 23.25, 23.26, 23.27; 422/89

[56] References Cited

U.S. PATENT DOCUMENTS

| | | | |
|---|---|---|---|
| 3,134,257 | 5/1964 | Reinecke | 73/23.35 |
| 3,206,968 | 9/1965 | Leggoe et al. | 73/23.42 |
| 3,240,052 | 3/1966 | Reinecke et al. | 73/23.1 |
| 3,298,786 | 1/1967 | Hinsvark | 422/89 |
| 3,405,551 | 10/1968 | Halasz | 73/23.1 |
| 3,879,984 | 4/1975 | Welland | 73/23.22 |
| 4,384,471 | 5/1983 | Wentzel | 422/89 |

FOREIGN PATENT DOCUMENTS

| | | | |
|---|---|---|---|
| 1212317 | 3/1966 | Germany . | |
| 2840612 | 3/1980 | Germany . | |
| 1236937 | 6/1971 | United Kingdom | 73/23.42 |
| 1291724 | 10/1972 | United Kingdom . | |

OTHER PUBLICATIONS

US-Z "Instrument News", vol. 19, 1969, No. 4, p. 16.

Primary Examiner—Hezron E. Williams
Assistant Examiner—Michael J. Brock
Attorney, Agent, or Firm—Kenyon & Kenyon

[57] ABSTRACT

A method for stabilizing a pressure differential in a first of two successive gas chromatographic separation columns of a valveless separation column arrangement includes the step of supplying a carrier gas at a controlled pressure to an inlet and outlet of the first separation column. Furthermore, the carrier gas pressure at the inlet of the first separation column is controlled by a command variable formed at least in part from a pressure at the outlet of the first separation column.

4 Claims, 1 Drawing Sheet

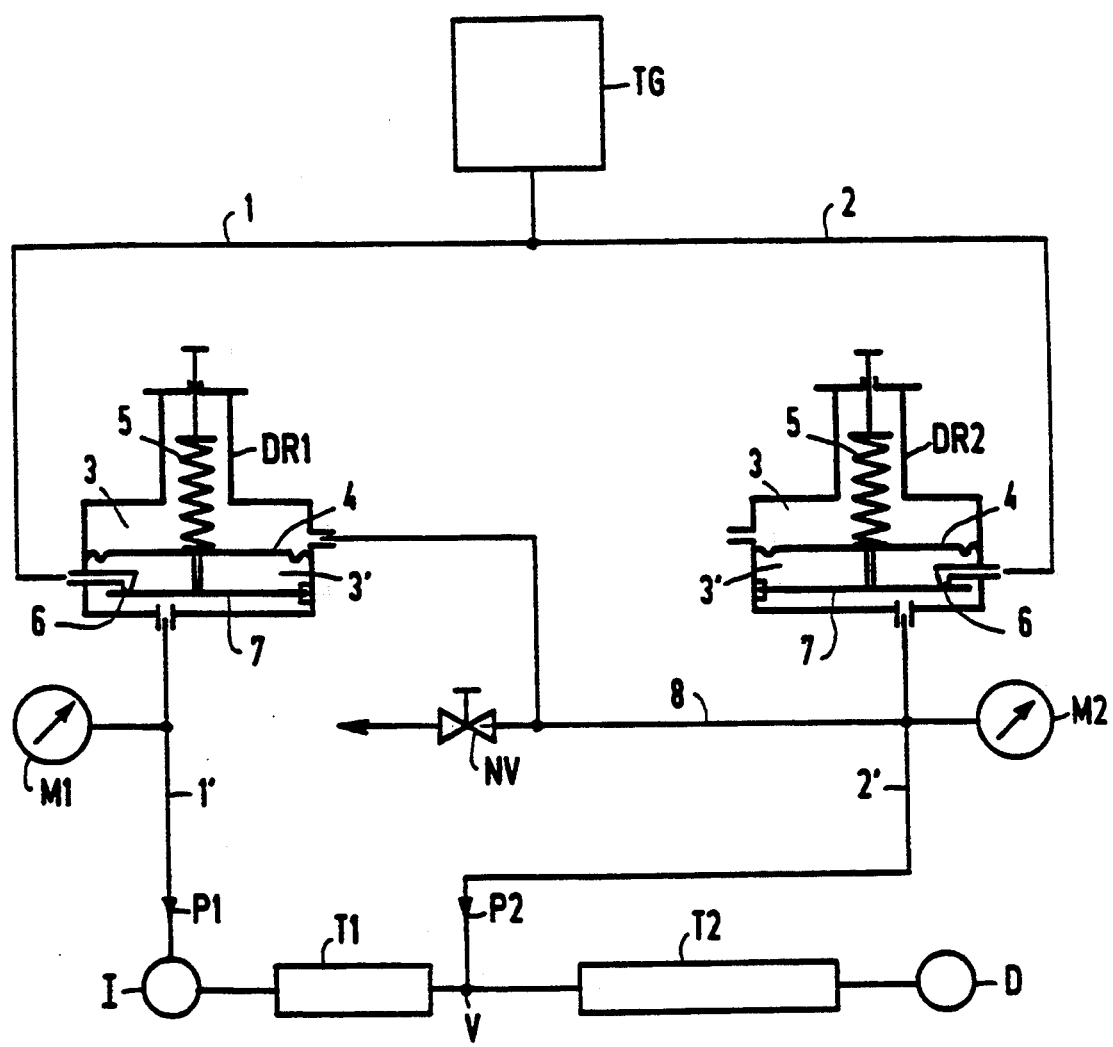

METHOD AND APPARATUS FOR REGULATING THE CARRIER GAS PRESSURE FOR SEPARATION COLUMN ARRANGEMENTS IN GAS CHROMATOGRAPHY

BACKGROUND OF THE INVENTION

The invention relates to a method and apparatus for regulating gas pressures and more particularly to a method and apparatus for regulating the carrier gas pressure in a valveless column arrangement.

Valveless separation column arrangements have two successive separations columns. In order to backwash the system, the direction of flow of the gas in the first separation column can be reversed by a pressure gradient that is produced by switching the carrier gas feed. Such a procedure is disclosed in FIG. 1 of "Instrument News", Vol. 19, 1969, No. 4, page 16. The carrier gas is supplied to the inlet of the first separation column via a sample injector and then to the junction between the two separation columns (i.e., to the outlet of the first column). The pressures in the two carrier gas feeds are adjustable by pressure regulators. When used in laboratory gas chromatography the instruments are operated at relatively constant ambient temperatures, while in process gas chromatography the instruments may be exposed to temperature fluctuations. Commercial, temperature-compensated gas pressure regulators have significant temperature fluctuations. For example, at an exit pressure of 2 bars and at room temperature (20° C.), there is an error of about 0.3% per 10° C. Furthermore, this error disproportionately increases at higher pressures. For example, the error at 3 bars is about 0.6% per 10° C.

The differential pressure decreasing in the valveless separation column arrangement over the first separation column determines the retention times of the column. Therefore, the differential pressure should be maintained as constant as possible.

Due to the differing fractional temperature errors occurring at different pressures, changes in the ambient temperature cause a variation in the differential pressure over the first column. Consequently, these differential pressure variations lead to retention time shifts, which because of the narrow peaks have an adverse effect on the desired result, particularly when high-performance capillary separation columns are used.

Accordingly, the problem in the prior art is the differential pressure acting in the first separation column is dependent of temperature and pressure-related deviations so that the retention times, which depend on the flow through the column, remain substantially constant.

SUMMARY OF THE INVENTION

The present invention provides a method and apparatus for stabilizing a pressure differential in a first of two successive gas chromatographic separation columns of a valveless separation column arrangement. The method of the invention includes the step of supplying a carrier gas at a controlled pressure to an inlet and outlet of the first separation column. Furthermore, the carrier gas pressure at the inlet of the first separation column is controlled by a command variable formed at least in part from a pressure at the outlet of the first separation column.

The present invention provides a cascade control system in which a gas pressure regulator functions as a master controller that is disposed in the feed line and which is coupled to the junction of the separation columns. The outlet pressure of the pressure regulator forms at least a fraction of the command variable for the other pressure regulator. It is thereby possible to reduce the retention time shift caused by the temperature error by about a power of ten in comparison to known independent controls that control the two carrier gas streams. As a result, even if fluctuations in the ambient temperature occur, the measured results are not invalidated.

BRIEF DESCRIPTION OF DRAWINGS

The sole FIGURE schematically illustrates the pressure control system constructed according to the principles of the invention.

DETAILED DESCRIPTION

The operation of valveless separation column arrangements is generally known. Such arrangements typically include a sample injector I, two successive separation columns T1 and T2, and a detector D. Those elements of the valveless separation column arrangement that are not relevant to the invention are not shown in the FIGURE for greater clarity. From the carrier gas source TG two line branches 1 and 2 lead to the inlets of the gas pressure regulators DR1 and DR2, respectively. Arranged in a housing of these known gas pressure regulators are two pressure chambers 3 and 3' separated by a diaphragm 4. A compression spring 5 acts on one side of the diaphragm 4 with a nominal pressure set by axial adjustment. Exit pressures $P_1$ and $P_2$, which act on the side of the diaphragms 4 opposite the compression spring 5, are generated by the nozzle-baffle plate systems 6 and 7 disposed in the regulators DR1 and DR2, respectively. The pressures $P_1$ and $P_2$ are set and monitored by the pressure gauges M1 and M2.

The carrier gas feed line 1' originating from the outlet of the pressure regulator DR1 is coupled to the inlet of the separation column T1 via a sample injector I, while the feed line 2' originating from the outlet of the pressure regulator DR2 is coupled to the junction V, which is disposed at the outlet of the first separation column T1.

The outlet of pressure regulator DR2 is coupled to the inlet-side of pressure chamber 3 of pressure regulator DR1 via a line 8. Thus, pressure regulator DR1 acts as a differential pressure regulator whose command variable, (i.e., the desired value) has a component determined by the spring 5 and a component determined by the pressure $P_2$.

An adjustable flow resistance device is disposed in a branch of line 8 leading to the atmosphere. This device may be a needle valve NV having a flow rate of several milliliters per minute to prevent a possible return flow from the gas pressure regulator DR1 into the feed line 2' during the operation of the system.

In a practical example, the pressure $P_1$ was 2 bars and the pressure $P_2$ was 1.5 bars, and hence the differential pressure over the first separation column T1 was 0.5 bar. Three components of a gas mixture were determined, both at the ambient temperature of 20° C. (room temperature) and at the ambient temperature of 45° C.

As can be seen from the experimental values given in the following tables, the retention times are substantially better maintained with the differential pressure control of the present invention than with the known arrangements.

Table A shows the deviations in the retention time that occur for a known arrangement of the carrier gas feeds with two independent gas pressure regulators, and Table B shows the corresponding values for the arrangement of the gas carrier feeds of the present invention.

TABLE A

| | Retention Time | | |
|---|---|---|---|
| | At 20° C. | At 45° C. | Maximum Deviation |
| Component 1 | 5.210 min | 5.370 min | +0.160 min |
| Component 2 | 10.335 min | 10.470 min | +0.125 min |
| Component 3 | 16.940 min | 17.110 min | +0.170 min |

TABLE B

| | Retention Time | | |
|---|---|---|---|
| | At 20° C. | At 45° C. | Maximum Deviation |
| Component 1 | 5.145 min | 5.125 min | +0.020 min |
| Component 2 | 10.335 min | 10.350 min | +0.015 min |
| Component 3 | 16.980 min | 17.005 min | +0.020 min |

As can be seen from the Tables, at an ambient temperature differential of approx. 25° C. the deviations of the retention times in Table B are only about 10% of the deviations in Table A.

What is claimed is:

1. A method for controlling carrier gas pressures in supply lines coupled to an input and output of a first of two serially connected gas-chromatic separating columns of a separating column circuit, said method comprising the step of controlling an input pressure of the first separating column as a function of its output pressure with the effect of maintaining constant the difference between the inlet and outlet pressure of the first separation column.

2. A method for stabilizing a pressure differential in a first of two successive gas chromatographic separation columns of a separation column arrangement comprising the step of:
   supplying a carrier gas at a controlled pressure to an inlet and outlet of the first separation column; and
   controlling the carrier gas pressure at the inlet of the first separation column in response to a command variable formed of a first variable and of the outlet pressure of the first separation column.

3. A separation column arrangement comprising:
   a first and second carrier gas supply line;
   a first gas pressure regulator disposed in said first carrier gas supply line;
   a first separating column having an input coupled to said first regulator by said first supply line;
   a second gas pressure regulator disposed in said second carrier gas supply line, said first and second regulators each formed by membrane regulators having a spring loaded membrane for mechanically adjusting a command variable;
   a second separating column coupled to said first separating column at a connecting point, said second regulator also coupled to said connecting point; and
   a coupling line coupling an output of said second regulator to an input of said first regulator so that said first regulator acts as a differential pressure regulator with a command variable formed of a first variable and an output pressure of said second regulator.

4. The separation column arrangement of claim 3 further comprising a needle valve disposed in a branch of said coupling line open to atmosphere, said needle valve limiting the gas flow through said branch.

* * * * *